United States Patent [19]

Sanchez

[11] 4,136,105

[45] Jan. 23, 1979

[54] MONOPEROXYCARBONATES

[75] Inventor: Jose Sanchez, Grand Island, N.Y.

[73] Assignee: Pennwalt Corporation, Philadelphia, Pa.

[21] Appl. No.: 851,741

[22] Filed: Nov. 15, 1977

Related U.S. Application Data

[63] Continuation of Ser. No. 427,293, Dec. 21, 1973.

[51] Int. Cl.² .................. C07C 69/00; C08L 69/00
[52] U.S. Cl. .................. 260/453 RZ; 260/862
[58] Field of Search ................... 260/453 RZ

[56] References Cited

U.S. PATENT DOCUMENTS

| | | | |
|---|---|---|---|
| 2,374,789 | 5/1945 | Strain | 260/453 RZ |
| 3,326,859 | 6/1967 | Seiner | 260/453 RZ |
| 3,344,126 | 9/1967 | Witman | 260/42.39 |

*Primary Examiner*—Elbert L. Roberts
*Assistant Examiner*—Robert C. Whittenbaugh
*Attorney, Agent, or Firm*—Plumley and Tyner

[57] ABSTRACT

O-Alkyl OO-(t-octyl) monoperoxycarbonates of the formula $[CH_3C(CH_3)_2CH_2C(CH_3)_2OOC(=O)O-]_nR$ where n is an integer from 1-4, such as OO-(1,1,3,3-tetramethylbutyl) O-methyl monoperoxycarbonate, and processes using such compounds as initiators for polymerizing ethylenically unsaturated monomers and as curing catalysts for curing unsaturated polyester resin compositions.

12 Claims, No Drawings

MONOPEROXYCARBONATES

This is a continuation, of application Ser. No. 427,293, filed Dec. 21, 1973.

BACKGROUND OF THE INVENTION (a) Field of the Invention

This invention relates to O-alkyl OO-(1,1,3,3-tetramethylbutyl) monoperoxy carbonates and their uses as free-radical polymerization initiators and as free-radical curing catalysts. In the interest of brevity, 1,1,3,3-tetramethylbutyl will be hereinafter usually referred to as t-octyl.

(b) State of the Art

While applicant is not aware of any prior art which reports any of the compounds of this invention or recognizes their superior properties as free-radical initiators and curing catalysts, several patents have disclosed monoperoxycarbonates.

For example, U.S. Pat. No. 2,374,789 prepares O-alkyl OO-alkyl peroxycarbonates from t-butyl and ethyl hydroperoxides. British Patent 1,104,336 discloses the use of O-alkyl OO-t-alkyl peroxycarbonates as initiators for vinyl polymerizations wherein the OO-t-alkyl group can contain up to 6 carbons as in t-hexyl (similar olefin polymerizations are disclosed in British Pat. No. 1,102,067). U.S. Pat. No. 3,326,859 discloses the use of O-alkyl OO-alkyl peroxycarbonates as initiators wherein the preferred OO-alkyl group is t-butyl, t-amyl or α-cumyl. They also list bismonoperoxycarbonates wherein the O-alkyl group is —CH$_2$—CH$_2$— or isopropyl and the OO-alkyl group is t-butyl or —C(CH$_3$)$_2$CH$_2$CH$_2$C(CH$_3$)$_2$—. Similar disclosures are found in U.S. Pat. No. 3,344,126 and Canadian Pat. 775,576. While the monoperoxycarbonates are broadly claimed in some of these patents, none of the invention compounds are reported.

There is a commercial need for free-radical initiators for use in polymerizing vinyl monomers which have activity between that of t-butyl peroxybenzoate (an industry standard peroxide used in ethylene, styrene and other vinyl polymerizations) and that of dibenzoyl peroxide (a lower temperature industrial initiator). Usually polymerization reactor design, and hence heat removal capacity, fixes the cycle time for commercial polymerization processes. Thus, if it is wished to vary the molecular weight (and consequently the physical properties) of the polymer produced, one changes the temperature of the process and selects a free-radical initiator which will decompose at a rate such that the cycle time of the process remains essentially the same. If it is desired to increase the molecular weight of a polymer such as polystyrene, a lower polymerization temperature can be selected and a free-radical initiator with a lower half-life can be employed to bring about the polymerization. Conversely, if one wants to decrease molecular weight, a higher temperature can be selected and an initiator with a greater half-life can be employed. The 10 hour half-life for dibenzoyl peroxide is at about 70° C., whereas that for t-butyl perbenzoate is about 110° C. Hence a large gap in 10 hour half-life activity temperature exists between these two commercially used free-radical initiators. The initiator needed should also be a liquid for ease of metering into the polymerization reactor (dibenzoyl peroxide is a solid) and should be at least as efficient (preferably more so) in polymerizing vinyl monomers as t-butyl peroxybenzoate.

There is also a need commercially for a free-radical curing catalyst for unsaturated polyester resins which will have greater activity (be faster) than t-butyl peroxybenzoate (also used commercially for curing polyester resins) and OO-t-butyl O-isopropyl monoperoxycarbonate (a known monoperoxycarbonate) and will have activity similar to that of dibenzoyl peroxide (an industry standard). The curing catalyst should desirably be a liquid for ease of dissolution in the curable resin. Since dibenzoyl peroxide is a solid (melting point 106°–108° C.), a liquid curing catalyst with similar activity would be advantageous.

BRIEF SUMMARY OF THE INVENTION

This invention broadly relates to:

(A) O-Alkyl OO-t-octyl monoperoxycarbonates of the general formula:

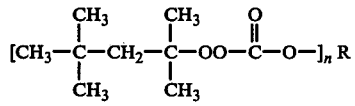

wherein:
(1) n is an integer from 1 to 4 (preferably 1);
(2) R is (broad preferred carbon ranges being given in parenthesis) selected from (when n is 1) alkyl (1–16), cycloalkyl (5–12, including mono-, bi- or tricycloalkyl), aryl (6–14), aralkyl (7–14), alkenyl (3–10), cycloalkenyl (5–10), alkynyl (3–14); (when n is 2) alkylene (2–12), cycloalkylene (4–12), arylene (6–14), alkenylene (2–12), alkynylene (4–12), methylenephenmethylene (8), methylenecyclohexylmethylene (8), —R$_1$XR$_1$—, —R$_2$YR$_2$—; (when n is 3) R$_3$C(CH$_2$—)$_3$, —HC(CH$_2$—)$_2$,

and (when n is 4) C(CH$_2$—)$_4$, the R groups being either unsubstituted or substituted with lower (1–4 carbon) alkyl, phenyl, furyl, halo (F, Cl, Br), cyano, nitro, carboxy, lower alkoxy, phenoxy, lower alkoxycarbonyl, phenoxycarbonyl, lower alkylcarbonyloxy, phenylcarbonyloxy, lower alkylsulfonyl, phenylsulfonyl, lower thioalkoxy, thiophenoxy or tertiary (preferably C$_4$–C$_8$) alkylperoxy substituent groups;
(3) R$_1$ is alkylene of 2–6 carbons;
(4) R$_2$ is phenylene;
(5) R$_3$ is alkyl of 1–5 carbons;
(6) X is —O— or —S—; and
(7) Y is —O—, —S—, —CH$_2$— or —C(CH$_3$)$_2$—; and (B) Improved processes using these monoperoxycarbonates (1) As initiators for polymerizing ethylenically unsaturated monomers (such as styrene) which are responsive at suitable temperatures to initiating amounts of free-radical polymerization initiators; and (2) As curing catalysts for curing unsaturated polyester resin compositions by heating in the presence of initiating amounts thereof.

DETAILED DESCRIPTION OF INVENTION

It has now been discovered that the subject O-alkyl OO-t-octyl monoperoxycarbonates have 10 hour half-lives close to the middle of the dibenzoyl peroxide/t-butyl perbenzoate range, that is at about 85°–90° C., and are usually liquids. In addition, they are found to be very efficient in high conversion vinyl polymerizations (such as in styrene) and to be very active in curing polyester resins.

Products

Examples of monoperoxycarbonates of this invention, in addition to those shown in the Examples to follow, include: O-methyl OO-t-octyl monoperoxycarbonate, O-propyl OO-t-octyl monoperoxycarbonate, O-isopropyl OO-t-octyl monoperoxycarbonate, O-dodecyl OO-t-octyl monoperoxycarbonate, O-neopentyl OO-t-octyl monoperoxycarbonate, O-(2-cyanoethyl) OO-t-octyl monoperoxycarbonate, O-(2-nitrobutyl) OO-t-octyl monoperoxycarbonate, O-(2-ethoxycarbonyl-1-methylethyl) OO-t-octyl monoperoxycarbonate, O-(2-acetoxy-1-methylethyl) OO-t-octyl monoperoxycarbonate, O-(2-benzoyloxyethyl) OO-t-octyl monoperoxycarbonate, O-(2-hexoxyethyl) OO-t-octyl monoperoxycarbonate, O-ethyl OO-t-octyl monoperoxycarbonate, O-(2-ethylhexyl) OO-t-octyl monoperoxycarbonate, O-sec-butyl OO-t-octyl monoperoxycarbonate, O-hexadecyl OO-t-octyl monoperoxycarbonate, O-(3-chloropropyl) OO-t-octyl monoperoxycarbonate, O-(1,2-dimethylpropyl) OO-t-octyl monoperoxycarbonate, O-carboxymethyl OO-t-octyl monoperoxycarbonate, O-(3-phenoxycarbonyl-1-methylpropyl) OO-t-octyl monoperoxycarbonate, O-(2-acetoxyethyl) OO-t-octyl monoperoxycarbonate, O-(2-butoxyethyl) OO-t-octyl monoperoxycarbonate, O-(2-phenoxyethyl) OO-t-octyl monoperoxycarbonate, O-(2-thioisopropoxyethyl) OO-t-octyl monoperoxycarbonate, O-(2-methylsulfonylethyl) OO-t-octyl monoperoxycarbonate, O-(2-adamantyl) OO-t-octyl monoperoxycarbonate, O-cyclopentyl OO-t-octyl monoperoxycarbonate, O-cyclododecyl OO-t-octyl monoperoxycarbonate, O-(2-methylcyclohexyl) OO-t-octyl monoperoxycarbonate, O-(2-ethoxycarbonylcyclopentyl) OO-t-octyl monoperoxycarbonate, O-phenyl OO-t-octyl monoperoxycarbonate, O-(2-naphthyl) OO-t-octyl monoperoxycarbonate, O-(2-thiophenoxyethyl) OO-t-octyl monoperoxycarbonate, O-(2-phenylsulfonylethyl) OO-t-octyl monoperoxycarbonate, O-(4-phenylcyclohexyl) OO-t-octyl monoperoxycarbonate, O-cyclohexyl OO-t-octyl monoperoxycarbonate, O-(3-methylcyclohexyl) OO-t-octyl monoperoxycarbonate, O-(3,3,5-trimethylcyclohexyl) OO-t-octyl monoperoxycarbonate, O-(2-chlorocyclohexyl) OO-t-octyl monoperoxycarbonate, O-(4-chlorophenyl) OO-t-octyl monoperoxycarbonate, O-(1-anthryl) OO-t-octyl monoperoxycarbonate, O-(3-nitrophenyl) OO-t-octyl monoperoxycarbonate, O-(4-carboxyphenyl) OO-t-octyl monoperoxycarbonate, O-benzyl OO-t-octyl monoperoxycarbonate, O-(1-phenylethyl) OO-t-octyl monoperoxycarbonate, O-(2-phenylethyl) OO-t-octyl monoperoxycarbonate, O-bornyl OO-t-octyl monoperoxycarbonate, O-isobornyl OO-t-octyl monoperoxycarbonate, O-(1,5-dimethyl-4-hexen-1-yl) OO-t-octyl monoperoxycarbonate, O-(2-cyclopenten-1-yl) OO-t-octyl monoperoxycarbonate, O-(2,4,5-trichlorophenyl) OO-t-octyl monoperoxycarbonate, O-(4-methoxycarbonylphenyl) OO-t-octyl monoperoxycarbonate, O-(4-methylbenzyl) OO-t-octyl monoperoxycarbonate, O-(4-chlorobenzyl) OO-t-octyl monoperoxycarbonate, O-(8-phenyloctyl) OO-t-octyl monoperoxycarbonate, O-(2-propen-1-yl) OO-t-octyl monoperoxycarbonate, O-(9-decen-1-yl) OO-t-octyl monoperoxycarbonate, O-(2-methyl-2-propen-1-yl) OO-t-octyl monoperoxycarbonate, O-(2-cyclohexen-1-yl) OO-t-octyl monoperoxycarbonate, O-(3,5,5-trimethyl-2-cyclohexen-1-yl) OO-t-octyl monoperoxycarbonate, O-(2-propynyl) OO-t-octyl monoperoxycarbonate, O-(2-butynyl) OO-t-octyl monoperoxycarbonate, 1,2-di-(t-octylperoxycarbonyloxy) ethane, 1,2-di-(t-octylperoxycarbonyloxy) propane, 1,4-di-(t-octylperoxycarbonyloxy) butane, 2,2-dimethyl-1,3-di-(t-octylperoxycarbonyloxy) propane, 1,6-di-(t-octylperoxycarbonyloxy) hexane, 1,12-di-(t-octylperoxycarbonyloxy) dodecane, 2,2,4,4-tetramethyl-1,3-di-(t-octylperoxycarbonyloxy) cyclobutane, O-(2-cyclodecen-1-yl) OO-t-octyl monoperoxycarbonate, O-(1-propyl-2-propynyl) OO-t-octyl monoperoxycarbonate, O-(1-undecyl-2-propynyl) OO-t-octyl monoperoxycarbonate, 1,4-di(t-octylperoxycarbonyloxy) cyclohexane, 1,7-di-(t-octylperoxycarbonyloxy) cyclododecane, 1,3-di-(t-octylperoxycarbonyloxy) benzene, 1,4-di-(t-octylperoxycarbonyloxy) naphthalene, 9,10-di-(t-octylperoxycarbonyloxy) anthracene, O-furfuryl OO-t-octyl monoperoxycarbonate, 1,2-di-(t-octylperoxycarbonyloxy)ethylene, 1,4-di-(t-octylperoxycarbonyloxy)-2-butene, 2,5-di-(t-octylperoxycarbonyloxy)-3-hexene, 1,4-di-(t-octylperoxycarbonyloxy)benzene, 1,12-di-(t-octylperoxycarbonyloxy)-6-dodecene, 1,4-di-(t-octylperoxycarbonyloxy)-2-butyne, 2,5-di-(t-octylperoxycarbonyloxy)-3-hexyne, 1,12-di-(t-octylperoxycarbonyloxy)-6-dodecyne, 1,3-di-(t-octylperoxycarbonyloxymethyl)benzene, 1,4-di-(t-octylperoxycarbonyloxymethyl)benzene, 1,4-di-(t-octylperoxycarbonyloxymethyl)cyclohexane, di-[2-(t-octylperoxycarbonyloxy)ethyl] ether, di-[2-(t-octylperoxycarbonyloxy)propyl] ether, di-[6-(t-octylperoxycarbonyloxy) hexyl] ether, di[2-(t-octylperoxycarbonyloxy)ethyl] sulfide, 1,2,3-tri-(t-octylperoxycarbonyloxy)propane, 1,2,6-tri-(t-octylperoxycarbonyloxy)hexane, di-[4-(t-octylperoxycarbonyloxy)phenyl] ether, di-[4-(t-octylperoxycarbonyloxy)phenyl]methane, 2,2-di-[4-(t-octylperoxycarbonyloxy)phenyl]propane, 1,1,1-tri-(t-octylperoxycarbonyloxymethyl)ethane, 1,1,1-tri-(t-octylperoxycarbonyloxymethyl)hexane, tetra-(t-octylperoxycarbonyloxymethyl)methane, O-(3-fluoropropyl) OO-t-octyl monoperoxycarbonate and O-(3-bromopropyl) OO-t-octyl monoperoxycarbonate.

Preparation of Products

The novel O-alkyl OO-(t-octyl) monoperoxycarbonates of this invention are preparable from alkyl chloroformates and t-octyl hydroperoxide by methods described in the art for the syntheses of known monoperoxycarbonates.

The alkyl chloroformates can be made by reacting excess phosgene with alcohols followed by subsequent removal of excess phosgene. The Table below summarizes typical alcohols which can be used to prepare the precursors (alkyl chloroformates) to the O-alkyl OO-t-octyl monoperoxycarbonates of this invention:

Table I

| Class | Alcohols Examples |
|---|---|
| Alcohols-saturated-acyclic | methanol, ethanol, n-propanol, isopropanol, n-butanol, sec-butanol, 2-pentanol, 2-methylbutanol, 3-methylbutanol, 2-ethylhexanol, dodecanol, hexadecanol, 1,2-dimethylpropanol |
| Alcohols-unsaturated-acyclic | allyl alcohol, methallyl alcohol, propargyl alcohol, crotyl alcohol |
| Alcohols-cyclic, bicyclic, tricyclic | cyclopentanol, cyclohexanol, 2-methylcyclohexanol, 3-methylcyclohexanol, 3,3,5-trimethylcyclohexanol, cyclododecanol, 2-cyclopentenol, 2-cyclohexenol, borneol, norborneol, isoborneol, |

Table I-continued

| Class | Alcohols<br>Examples |
|---|---|
| Alcohol-<br>substituted | 2-adamantanol<br>3-chloropropanol, 2-cyanoethanol, 2-chloroethanol, 2-nitrobutanol, glycolic acid, 1-ethoxycarbonyl-2-propanol, 4-phenoxycarbonyl-2-butanol, 1-acetoxy-2-propanol, 2-acetoxyethanol, 2-hexoxyethanol, 2-phenoxyethanol, 2-thioisopropoxyethanol, thiophenoxyethanol, 2-methylsulfonylethanol, 2-phenylsulfonylethanol, 4-phenylcyclohexanol, 2-chlorocyclohexanol, 2-ethoxycarbonylcyclopentanol |
| Aryl alcohols<br>(phenols) | phenol, 1-naphthol, anthrol, m-cresol, 4-t-butylphenol |
| Aryl alcohols-<br>substituted | p-chlorophenol, 2,4,5-trichlorophenol, 4-hydroxybenzoic acid, 4-methoxycarbonylphenol, pentachlorophenol, m-nitrophenol |
| Aralkyl alcohols | benzyl alcohol, p-methylbenzyl alcohol, p-chlorobenzyl alcohol, methyl phenyl carbinol, 2-phenylethanol, 8-phenyloctanol |
| Diols, Triols,<br>Polyols | ethylene glycol, propylene glycol, 1,4-butanediol, 2,2-dimethyl-1,3-propanediol, 1,6-hexanediol, 1,12-dodecanediol, 2,2,4,4-tetramethyl-1,3-cyclobutanediol, 1,4-cyclohexanediol, 1,7-cyclododecanediol, 1,4-di(hydroxymethyl)cyclohexane, 2-butene-1,4-diol, 2-butyne-1,4-diol, diethylene glycol, dipropylene glycol, di-(2-hydroxyethyl) sulfide, 4,4'-isopropylidenediphenol, 1,4- |
| Diols, Triols,<br>Polyols | dihydroxybenzene, 1,4-dihydroxynaphthalene, 1,4-di(hydroxymethyl)benzene, 2,2-di(hydroxymethyl)propanol, 1,2,6-hexanetriol, pentaerythritol, glycerol |

The chloroformates from diols, triols and polyols can be prepared by the processes outlined in Canadian Patent 764,975.

Polymerization

In the free-radical initiated polymerizations or copolymerizations of ethylenically unsaturated monomers at suitable temperatures (and pressures), the invention O-alkyl OO-t-octyl monoperoxycarbonates are found to provide improved efficiencies on weight and equivalent bases when they are compared to known O-alkyl OO-t-butyl monoperoxycarbonates, such as OO-t-butyl O-isopropyl monoperoxycarbonate, similarly employed.

Ethylenically unsaturated monomers include olefins, such as ethylene, propylene, styrene, alpha-methylstyrene, chlorostyrene, vinyltoluene, vinyl pyridine and divinylbenzene; diolefins, such as 1,3-butadiene, isoprene and chloroprene; vinyl esters, such as vinyl acetate, vinyl propionate, vinyl laurate, vinyl benzoate and divinyl carbonate; unsaturated nitriles, such as acrylonitrile and methacrylonitrile; acrylic acid, methacrylic acid and their esters and amides, such as methyl, ethyl, n-butyl and 2-ethylhexyl acrylates and methacrylates, and acrylamide and methacrylamide; maleic anhydride; maleic and fumaric acids and their esters; vinyl halo and vinylidene halo compounds, such as, vinyl chloride, vinyl bromide, vinyl fluoride, vinylidene chloride and vinylidene fluoride; perhalo olefins, such as tetrafluoroethylene, hexafluoropropylene and chlorotrifluoroethylene; vinyl ethers, such as methyl vinyl ether, ethyl vinyl ether and n-butyl vinyl ether; allyl esters, such as allyl acetate, allyl benzoate, diallyl phthalate, allyl ethyl carbonate, triallyl phosphate, diallyl fumarate and diallyl carbonate; acrolein; methyl vinyl ketone; and mixtures thereof.

Temperatures of about 50° C. to 250° C. and peroxide levels of about 0.005% to 5% or more by weight, based on monomer, are normally employed in the polymerizations. Conventional solvents (e.g., benzene) may be optionally added to the reaction system.

Curing of Unsaturated Polyester Resins

In curing of unsaturated polyester resin compositions by heating at suitable curing temperatures in the presence of free-radical polymerization initiators, the use of the O-alkyl OO-t-octyl monoperoxycarbonates of this invention are found to give faster cures (that is, they have greater activities) than do t-butyl peroxybenzoate (a peroxyester used commercially for curing of unsaturated polyester resins) and known O-alkyl OO-t-butyl monoperoxycarbonates such as OO-t-butyl O-isopropyl monoperoxycarbonate.

Unsaturated polyester resins that can be cured by the peroxides of this invention usually consist of an unsaturated polyester and one or more polymerizable monomers.

The unsaturated polyesters are, for instance, polyesters as they are obtained by esterifying at least one ethylenically unsaturated di- or polycarboxylic acid, anhydride or acid halide, such as maleic acid, fumaric acid, glutaconic acid, itaconic acid, mesaconic acid, citraconic acid, allylmalonic acid, allylsuccinic acid, tetrahydrophthalic acid and others with saturated or unsaturated di- or polyols, such as ethylene glycol, diethylene glycol, triethylene glycol, 1,2- and 1,3-propanediols, 1,2-, 1,3- and 1,4-butanediols, 2,2-dimethyl-1,3-propanediol, 2-hydroxymethyl-2-methyl-1,3-propanediol, 2-buten-1,4-diol, 2-butyn-1,4-diol, 2,2,4-trimethyl-1,3-pentanediol, glycerol, pentaerythritol, mannitol and others. Mixtures of such polyacids and/or mixtures of such polyalcohols may also be used. The unsaturated di-or polycarboxylic acids may be replaced, at least partly, by saturated polycarboxylic acids, such as adipic acid, succinic acid, sebacic acid and others and/or by aromatic polycarboxylic acids, such as phthalic acid, trimellitic acid, pyromellitic acid, isophthalic acid and terephthalic acid. The acids used may be substituted by groups such as halogen. Examples of such suitable halogenated acids are, for instance, tetrachlorophthalic acid, 2,3-dicarboxy-1,4,5,6,7,7-hexachlorobicyclo(2.2.1)-2-heptene and others.

The other component of the unsaturated polyester resin composition, the polymerizable monomer or monomers, can be preferably ethylenically unsaturated monomers, such as styrene, chlorostyrene, vinyltoluene, divinylbenzene, alpha-methystyrene, diallyl maleate, diallyl phthalate, dibutyl fumarate, acrylonitrile, triallyl phosphate, triallyl cyanurate, methyl acrylate, methyl methacrylate, n-butyl methacrylate, ethyl acrylate and others, or mixtures thereof, which are copolymerizable with said polyesters.

A preferred resin composition contains as the polyester component the esterification product of 1,2-propylene glycol (a polyalcohol), maleic anhydride (an anhydride of an unsaturated polycarboxylic acid) and phthalic anhydride (an anhydride of an aromatic dicarboxylic acid) as well as the monomer component, styrene.

Temperatures of about 20° C. to 200° C. and peroxide levels of about 0.05% to 5% or more by weight of curable unsaturated polyester resin are normally employed.

Fillers such as carbon blacks, silicas, clays, aluminum silicates, alkali and alkaline earth metal carbonates, glass spheres (hollow or solid), titanium dioxide ($TiO_2$), mold release agents and water can optionally be added to the curable unsaturated polyester resin. Up to 60% or more by weight of these fillers can be used. In addition, blowing agents can be added to foam the resin. Example VIII below illustrates a mold curing application using such fillers.

The O-alkyl OO-t-octyl monoperoxycarbonates of this invention can be employed for vulcanizing natural and synthetic rubbers, for curing of olefin copolymers and terpolymers, such as EPR (ethylene-propylene copolymer) and EPDM (ethylene-propylene-diene terpolymer), for crosslinking of PE (polyethylene), ethylene-vinyl acetate copolymers, silicon rubbers, styrene-butadine rubbers and the like, in the presence or absence of additives and fillers, such as sulfur, carbon blacks, silicas, clays, carbonates, antioxidants, heat and light stabilizers, sensitizers, dyes, accelerators, zinc oxide, oils, blowing agents, etc.

EXAMPLES

The following examples further illustrate the subject invention but are not in limitation thereof.

EXAMPLE I

Preparation of OO-(1,1,3,3-Tetramethylbutyl) O-Methyl Monoperoxycarbonate

A jacketed reactor equipped with an efficient mechanical stirrer, a therometer and a dropping funnel was charged with 10 g. of 20% aqueous sodium hydroxide solution. The solution was vigorously stirred at 15° C. to 20° C. while 7.8 g. (0.048 mole) of 91.3% 1,1,3,3-tetramethylbutyl hydroperoxide was slowly added. After the addition was completed, the resulting solution was cooled to 10° C. and 4.3 g. (0.045 mole) of methyl chloroformate was added slowly over a 15 to 20 min. period to the vigorously stirred solution. The reaction mixture was stirred for an additional 30 min. at 5° C. to 10° C. after which 30 ml. of diethyl ether was added. The organic phase was separated, washed with 20% aqueous sodium hydroxide solution, then with water to neutral and then dried over anhydrous sodium sulfate. After separation of the desiccant, the ether was removed in vacuo leaving 8.7 g. of liquid which had an assay of 91% according to "active oxygen" content. The corrected yield was 86.3%.

EXAMPLE II

Syntheses of Other O-Alkyl OO-(1,1,3,3-Tetramethylbutyl) Monoperoxycarbonates

Following essentially the same procedure as that described in Example I other O-alkyl OO-(1,1,3,3-tetramethylbutyl) monoperoxycarbonates were prepared from 1,1,3,3-tetramethylbutyl hydroperoxide and other alkyl chloroformates. The synthetic data (yields and assays) are summarized in Example II Table. Also, in the table are the results from Example I. In general, the O-alkyl OO-t-octyl monoperoxycarbonates were liquids at room temperature [the words OO-(1,1,3,3-tetramethylbutyl) and t-octyl are synonymous and are used interchangeably in Example II Table].

TABLE

| No. | Chloroformate (CF)[1.] | O-Alkyl OO-(1,1,3,3-Tetramethylbutyl) Monoperoxycarbonates | Assay, % | Corr. Yield, % |
|---|---|---|---|---|
| C-1 | methyl CF (Example I) | O-methyl OO-t-octyl monoperoxycarbonate | 91.0 | 86.3 |
| C-2 | ethyl CF | O-ethyl OO-t-octyl monoperoxycarbonate | 95.3 | 78.6 |
| C-3 | n-propyl CF | O-n-propyl OO-t-octyl monoperoxycarbonate | 95.1 | 61.0 |
| C-4 | isopropyl CF | O-isopropyl OO-t-octyl monoperoxycarbonate | 96.4 | 80.2 |
| C-5 | n-butyl CF | O-n-butyl OO-t-octyl monoperoxycarbonate | 95.5 | 81.0 |
| C-6 | sec-butyl CF | O-sec-butyl OO-t-octyl monoperoxycarbonate | 93.6 | 70.3 |
| C-7 | 1-methylbutyl CF | O-(1-methylbutyl) OO-t-octyl monoperoxycarbonate | 94.4 | 78.0 |
| C-8 | 2-methylbutyl CF | O-(2-methylbutyl) OO-t-octyl monoperoxycarbonate | 93.8 | 73.5 |
| C-9 | 3-methylbutyl CF | O-(3-methylbutyl)OO-t-octyl monoperoxycarbonate | 92.6 | 48.2 |
| C-10 | 2-ethylhexyl CF | O-(2-ethylhexyl) OO-t-octyl monoperoxycarbonate | 89.5 | 62.5 |
| C-11 | n-dodecyl CF | O-(n-dodecyl)OO-t-octyl monoperoxycarbonate | 89.9 | 75.3 |
| C-12 | 2-methylcyclohexyl CF | O-(2-methylcyclohexyl) OO-t-octyl monoperoxycarbonate | 90.5 | 73.0 |
| C-13 | 3-methylcyclohexyl CF | O-(3-methylcyclohexyl) OO-t-octyl monoperoxycarbonate | 94.3 | 69.2 |
| C-14 | 1,5-dichlorocarbonyl-oxypentane | 1,5-di-(t-octylperoxycarbonyloxy)-pentane | 90.0 | 60.0 |
| C-15 | 3-chloropropyl CF | O-(3-chloropropyl) OO-t-octyl monoperoxycarbonate | 70.8 | 56.7 |
| C-16 | 2,2,2-trichloroethyl CF | O-(2,2,2-trichloroethyl) OO-t-octyl monoperoxycarbonate | 95.3 | 50.0 |
| C-17 | 2-phenoxyethyl CF | O-(2-phenoxyethyl) OO-t-octyl monoperoxycarbonate | 82.0 | 73.4 |
| C-18 | 2-hexoxyethyl CF | O-(2-hexoxyethyl) OO-t-octyl monoperoxycarbonate | 83.0 | 83.0 |
| C-19 | di(2-chlorocarbonyl-oxyethyl) sulfide | di-[2-(t-octylperoxycarbonyloxy)-ethyl] sulfide | 72.8 | 68.0 |
| C-20 | cyclohexyl CF | O-cyclohexyl OO-t-octyl monoperoxycarbonate | 82.8 | 57.8 |
| C-21 | 1,3-dimethyl-3-(t-butylperoxy)-butyl CF | O-(1,3-dimethyl-3-(t-butylperoxy)-butyl) OO-t-octyl monoperoxycarbonate | 96.5 | 72.0 |

[1.]The appropriate chloroformate was prepared by reacting the corresponding alcohol or polyol with phosgene

EXAMPLE III

100° C. (212° F.) SPI Exotherms of O-Alkyl OO-t-Octyl Monoperoxycarbonates

The unsaturated polyester resins employed in this example was a mixture of an unsaturated polyester and styrene monomer.

The unsaturated polyester was an alkyd resin made by esterifying the following components:

| Component | Quantity |
| --- | --- |
| Maleic anhydride | 1.0 mole |
| Phthalic anhydride | 1.0 mole |
| Propylene glycol | 2.2 moles |

To the resulting resin was added 0.013% by weight of hydroquinone inhibitor. The alkyd resin had an Acid No. of 45–50. Seven (7) parts by weight of the above polyester (alkyd resin) was diluted with three (3) parts by weight of monomeric styrene. The resulting unsaturated polyester resin had the following properties:

a. Viscosity (Brookfield No. 2 at 20 r.p.m.) — 13.08 poise
b. Specific gravity — 1.14

Curing Procedure

Gelation and cure charcteristics of various initiators in the above unsaturated polyester resin were determined using the Standard SPI Exotherm Procedure ("SPI Procedure for Running Exotherm Curves-Polyester Resins", published in the Preprint of the 16th Annual Converence - Reinforced Plastics Division, Society of the Plastics Industry, Inc., February, 1961).

Using this procedure at 100° C. (212° F.) several O-alkyl OO-t-octyl monoperoxycarbonates, OO-t-butyl O-isopropyl monoperoxycarbonate (a known monoperoxycarbonate), t-butyl peroxybenzoate (a peroxyester used commercially for curing unsaturated polyester resins) and dibenzoyl peroxide (a standard curing catalyst) were evaluated as curing catalyst at "active oxygen" levels equivalent to 1.0% dibenzoyl peroxide. The results are summarized in Example III Table. The results show that the O-alkyl OO-t-octyl monoperoxycarbonates are significantly faster than OO-t-butyl O-isopropyl monoperoxycarbonate and t-butyl peroxybenzoate and are almost as fast as dibenzoyl peroxide.

TABLE

100° C (212° F) SPI Exotherms of O-Alkyl OO-t-Octyl Monoperoxycarbonates (at "active oxygen" levels equal to 1.0% by wt. of dibenzoyl peroxide)

| Curing Catalyst | Gel. Min. | Cure. Min. | Peak °F | Barcol |
| --- | --- | --- | --- | --- |
| C-1 | 4.9 | 6.6 | 420 | 40 |
| C-2 | 2.5 | 3.6 | 430 | 45 |
| C-3 | 2.4 | 3.5 | 430 | 45 |
| C-4 | 2.4 | 3.5 | 430 | 45 |
| C-5 | 2.6 | 3.7 | 430 | 45 |
| C-7 | 2.2 | 3.3 | 432 | 45 |
| C-8 | 2.5 | 3.5 | 430 | 45 |
| C-9 | 2.3 | 3.4 | 430 | 45 |
| C-12 | 2.0 | 2.7 | 427 | 45 |
| C-13 | 2.4 | 3.4 | 432 | 45 |
| OO-t-butyl O-isopropyl monoperoxycarbonate | 6.6 | 8.8 | 415 | 40–45 |
| t-butyl peroxybenzoate | 14.1 | 16.8 | 405 | 40–45 |
| dibenzoyl peroxide | 2.0 | 3.1 | 424 | 45 |

EXAMPLE IV

100° C. (212° F.) SPI Exotherms of OO-t-Alkyl O-n-Propyl Monoperoxycarbonates The unsaturated polyester resin and the procedure employed in Example III were employed in this example. Example IV Table summarized 100° C. SPI Exotherm data for OO-t-alkyl O-n-propyl monoperoxycarbonates (preparable from n-propyl chloroformates and hydroperoxides and dihydroperoxides) at "active oxygen" levels equivalent to 1% dibenzoyl peroxide.

EXAMPLE IV Table

100° C (212° F) SPI Exotherms of OO-t-Alkyl O-n-Propyl Monoperoxycarbonate (at "active oxygen" levels equal to 1.0% by wt. of dibenzoyl peroxide)

| OO-t-Alkyl Group | Gel, Min. | Cure, Min. | Peak, °F | Barcol |
| --- | --- | --- | --- | --- |
| t-Butyl | 6.7 | 9.1 | 422 | 40–50 |
| t-Amyl | 5.8 | 7.2 | 425 | 45 |
| 1,1,4,4-Tetramethylbutylene | 5.2 | 7.2 | 428 | 45 |
| t-Octyl (C-3) | 2.4 | 3.5 | 430 | 45 |
| dibenzoyl peroxide | 2.0 | 3.1 | 424 | 45 |

These results show that the t-octyl derivatives (peroxides of this invention) are considerably faster in curing the unsaturated polyester resin than are OO-t-alkyl O-n-propyl monoperoxycarbonates prepared from other hydroperoxides and dihydroperoxides.

EXAMPLE V

82° C. (180° F.) SPI Exotherms of OO-t-Alkyl O-Isopropyl Monoperoxycarbonates The unsaturated polyester resin and procedure employed in Example III were employed in this example. Example V Table summarizes 82° C. (180° F.) SPI Exotherm data for OO-t-alkyl O-isopropyl monoperoxycarbonates (prepared from isopropyl chloroformate and various hydroperoxides) at "active oxygen" levels equivalent to 1.0% dibenzoyl peroxide.

EXAMPLE V Table

82° C (180° F) SPI Exotherms of OO-t-Alkyl O-Isopropyl Monoperoxycarbonates (at "active oxygen" levels equal to 1.0% by wt. of dibenzoyl peroxide)

| OO-t-Alkyl Group | Gel. Min. | Cure, Min. | Peak, °F | Barcol |
| --- | --- | --- | --- | --- |
| t-Butyl | >30.0 | — | — | — |
| t-Amyl | 12.6 | 16.2 | 335 | 15–20 |
| t-Hexyl[1] | 14.7 | 17.5 | 340 | 20–25 |
| 1-Methylcyclohexyl | 7.6 | 11.7 | 365 | 10–20 |
| t-Octyl (C-4) | 4.1 | 6.3 | 375 | 25–30 |
| Dibenzoyl peroxide | 4.0 | 5.8 | 395 | 40–45 |

[1] t-Hexyl is 3-Methyl-3-pentyl.

These results show that at 82° C. the OO-t-octyl derivatives (peroxides of this invention) are considerably faster in curing the unsaturated polyester resin than are similar OO-t-alkyl O-alkyl monoperoxycarbonates of the art. In fact, (C-4) is almost as fast as dibenzoyl peroxide. Since the OO-t-hexyl derivative is slower than the OO-t-amyl derivative, it was unexpected that the OO-t-octyl derivative should be faster in curing the unsaturated polyester resin than the OO-t-hexyl derivative.

EXAMPLE VI

High Conversion Styrene Bulk Polymerization Efficiencies of O-Alkyl OO-t-Octyl Monoperoxycarbonates at 85° C./6.45 hrs.

For each free-radical initiator evaluated, a series of Pyrex glass tubes was filled with styrene solutions containing varying amounts of the free-radical initiator and sealed. Several tubes were used for each initiator. Amounts of the free-radical initiators in the tubes were adjusted so that the resulting % conversion versus concentration plots would cross 90% conversion after 6.45 hours at 85° C. After 6.45 hours at 85° C., the tubes were removed from the thermostatted bath and quickly chilled to −20° C. to prevent post-polymerization. The sealed tubes were then broken and their contents were dissolved in benzene. Each benzene solution was then poured into a large amount of methanol and the resulting precipitated polymer was separated by filtration, dried in an oven at 50°–55° C. and weighed. The % conversion of styrene to polymer was then determined and plots of initiator level versus % conversion were constructed. The initiator levels (in weight and equivalence units) required to achieve 90% conversion of styrene at 85° C. for 6.45 hours relative to those of OO-t-butyl O-isopropyl monoperoxycarbonate (a known monoperoxycarbonate) were determined for several of the O-alkyl OO-t-octyl monoperoxycarbonates of this invention. The weight and equivalent efficiencies ("W" and "E", respectively) of the O-alkyl OO-t-octyl monoperoxycarbonates of this invention relative to those of OO-t-butyl O-isopropyl monoperoxycarbonate are summarized in Example VI Table. The lower the values of "W" and "E",

EXAMPLE IV

Table

| 85° C/6.45 hours High Conversion Styrene Polymerization Efficiencies | | | |
|---|---|---|---|
| | | Efficiencies | |
| Initiator | % Conversion | "E" | "W" |
| (C-1) | 90 | 0.49 | 0.57 |
| (C-3) | 90 | 0.31 | 0.43 |
| (C-4) | 90 | 0.31 | 0.41 |
| OO-t-Butyl O-isopropyl Monoperoxycarbonate | 90 | 1.00 | 1.00 |

The greater the efficiencies on weight and equivalent bases, respectively. The data in Example VI Table show that the monoperoxycarbonates of this invention [(C-1), (C-3) and (C-4)] are significantly more efficient on weight and equivalent bases than is OO-t-butyl O-isopropyl monoperoxycarbonate, a known monoperoxycarbonate.

EXAMPLE VII

Use of C-21 to Prepare a Styrene/Methyl Methacrylate (Styrene/MMA) Block Copolymer Preparation of a Styrene Telechelic Polymer A Pyrex tube was charged with 5.0g. of distilled styrene and 0.259g. of C-21 (96.5% assay). After sealing with a flame, the tube was placed in a 75° C. bath for 8 hours. The tube and its contents were then cooled to room temperature and, after opening the tube, the resulting polymer was dissolved in 100 ml. of benzene. The polymer was then precipitated by adding the benzene solution slowly to 1000ml. of methanol. After isolation of the polymer dissolution in 100 ml. of benzene and precipitation from 1000ml. of methanol was repeated twice more. After separation of the polymer by filtration and subsequently drying in an oven at 50°–55° C., 4.2g. of styrene telechelic polymer was obtained.

Preparation of a Styrene/Methyl Methacrylate Block Copolymer

A Pyrex tube was charged with 2.0g. of methyl methacrylate (MMA) and 1.0g. of the above styrene telechelic polymer. The tube was sealed and placed in a 115° C. bath for 3 hours. The tube and its contents were then cooled to room temperature and the resulting solid Styrene/MMA block copolymer was removed and pulverized with a hammer. The yield was 3.0g.

Evaluation of the Styrene/MMA Block Copolymer

Chloroform solutions of styrene homopolymer, methyl methacrylate (MMA) homopolymer and the Styrene/MMA block copolymer (described above) were prepared. Each had 13% solids (polymer) content. In a control experiment, 2.0g. each of the styrene homopolymer solution and the MMA homopolymer solution were thoroughly mixed and the demix time (time required for complete phase separation) was noted. In the test experiment 2.0g. each of the styrene homopolymer solution, the MMA homopolymer solution and the Styrene/MMA block copolymer solution were thoroughly mixed and the demix time was noted. The resulting data are summarized in Example VII Table and show that a Styrene/MMA block copolymer was formed by reacting the above Styrene telechelic polymer with MMA and that it was useful for compatibilizing styrene homopolymer and MMA homopolymer mixtures.

EXAMPLE VII

Table

| Demix Tests | Control Experiment | Test Experiment |
|---|---|---|
| Styrene homopolymer soln. | 2.0g. | 2.0g. |
| MMA homopolymer soln. | 2.0g. | 2.0g. |
| Styrene/MMA Block Copolymer soln. | 0.0g. | 2.0g. |
| Solids content of resulting mixture | 13% | 13% |
| Demix Time | 30–60 mins. | > 312 hrs. |

EXAMPLE VIII

250° F. Mold Curing of Unsaturated Polyester Resins Catalyzed with O-Alkyl OO-t-Alkyl Monoperoxycarbonates The unsaturated polyester resin described in Example III was employed in this example. To 60 parts by weight of the resin was added 0.5 parts by weight of Zelec ® UN (an organic phosphate release agent). Then 35 parts by weight of ASP-400 (hydrous aluminum silicates) and 5 parts by weight of $TiO_2$ were mixed into the resin for 15 minutes. This gave the molding resin. Prior to mold curing 1.0% by weight of the curing catalyst was blended into the molding resin. During the molding operation, two layers of glass mats were employed to reinforce the cured molding resin. The cured laminate was then composed of 28% by weight of glass mat and 72% by weight of molding resin.

Mold Curing Procedure

One layer of glass mat was placed in the mold. The molding resin containing 1.0% by weight of catalyst was then weighed onto a second glass mat which was then placed in the mold. A thermocouple was placed between the two glass mats and the press was closed. The laminates were cured at 250° F. and at a mold pressure of 735 p.s.i. (25 tons) on the laminates. The cure time, the peak exotherm and the Barcol hardness were determined by the procedures used in Example III. The platen gel time was obtained by placing about 5g. of the molding resin onto the hot lower mold surface at 250° F. and observing the time required to gel the molding resin.

Following this procedure several of the O-alkyl OO-t-octyl monoperoxycarbonates and other known monoperoxycarbonates were evaluated as mold curing catalysts. The resulting data are summarized in Example VIII Table and show that the O-alkyl OO-t-octyl monoperoxycarbonates of this invention give much faster cures of the molding resin than do known monoperoxycarbonates.

Table

250° F Mold Curing by O-Alkyl OO-t-Alkyl Monoperoxycarbonates (1% by wt. of peroxide)

| Invention Designation | OO-t-Alkyl | O-Alkyl | Platen Gel. secs. | Cure, Mins. | Peak Exo., °F | Barcol |
|---|---|---|---|---|---|---|
| C-4 | t-Octyl | Isopropyl | 13 | 0.60 | 297 | 60 |
| C-2 | t-Octyl | Ethyl | 13 | 0.60 | 290 | 60 |
| C-12 | t-Octyl | 2-Methylcyclohexyl | 12 | 0.65 | 297 | 60 |
| * | t-Amyl | Isopropyl | 17 | 0.85 | 303 | 60 |
| * | t-Butyl | Isopropyl | 24 | 0.90 | 294 | 60–65 |

*Known O-alkyl OO-t-alkyl monoperoxycarbonates.

What is claimed is:

1. A compound of the formula

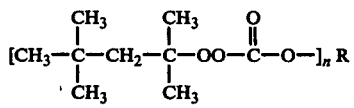

where
n is 1; and
R is alkyl of 3–16 carbon atoms or cycloalkyl of 5–12 carbon atoms; or
n is 2; and
R is alkylene of 2–12 carbon atoms or —$R_1$ XR —;

$R_1$ is alkylene of 2–6 carbon atoms; and $X^1$ is —O— or —S—.

2. A compound as in claim 1 wherein R is n-propyl.
3. A compound as in claim 1 wherein R is isopropyl.
4. A compound as in claim 1 wherein R is n-butyl.
5. A compound as in claim 1 wherein R is sec-butyl.
6. A compound as in claim 1 wherein R is 3-methylbutyl.
7. A compound as in claim 1 wherein R is cyclohexyl.
8. A compound as in claim 1 wherein n is 2 and R is alkylene of 2–12 carbons or —$R_1XR_1$—.
9. A compound as in claim 1 where n is 1; and
R is alkyl of 3–16 carbon atoms or cycloalkyl of 5–12 carbon atoms.
10. A compound of the formula

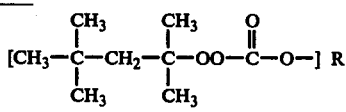

where
R is 1,3-dimethyl-3-(t-butylperoxy)butyl.
11. A compound as in claim 1 wherein R is pentamethylene (—$CH_2CH_2CH_2CH_2CH_2$—).

12. A compound as in claim 1 wherein R is 3-thiapentamethylene (—$CH_2CH_2SCH_2CH_2$—).

* * * * *